United States Patent [19]

Campbell

[11] Patent Number: 4,514,400

[45] Date of Patent: * Apr. 30, 1985

[54] CARDIOTONIC 5-HETEROARYL-PYRIDONE

[75] Inventor: Henry F. Campbell, Lansdale, Pa.

[73] Assignee: William H. Rorer, Inc., Fort Washington, Pa.

[*] Notice: The portion of the term of this patent subsequent to Feb. 21, 2001 has been disclaimed.

[21] Appl. No.: 314,692

[22] Filed: Oct. 26, 1981

[51] Int. Cl.³ ............... A61K 31/495; A61K 31/505; C07D 401/00
[52] U.S. Cl. .................. 514/252; 514/256; 544/238; 544/333; 544/405
[58] Field of Search ............ 544/333, 405, 238; 424/250, 251

[56] References Cited

U.S. PATENT DOCUMENTS

| 4,107,315 | 8/1978 | Lesher et al. | 424/263 |
| 4,304,775 | 12/1981 | Lesher et al. | 544/238 |

FOREIGN PATENT DOCUMENTS 2070606A 9/1981 United Kingdom ............... 544/333

*Primary Examiner*—Donald G. Daus
*Assistant Examiner*—Cecilia Shen
*Attorney, Agent, or Firm*—James A. Nicholson; Alexis Barron; Martin F. Savitzky

[57] ABSTRACT

5-Heteroaryl-pyridone compounds, their pharmaceutical uses and a method of treating congestive heart failure are disclosed.

11 Claims, No Drawings

CARDIOTONIC 5-HETEROARYL-PYRIDONE

BACKGROUND OF THE INVENTION

1. Field of the Invention

This invention relates to novel 5-substituted-2(1H)-pyridones, useful as cardiotonic agents and for the treatment of congestive heart failure, to their preparation and to the compositions thereof.

2. Description of the Prior Art

British Pat. No. 1,322,318, published July 4, 1973, iscloses as intermediates 1,2-dihydro-2-oxo-6-(4- or pyridinyl)nicotinonitrile, 6-(4- or 3-pyridinyl)-2(1H)-pyridone.

U.S. Pat. No. 4,107,315 of Lesher et al relates to pyridinyl)-2(1H)-pyridones which are useful as cardiotonic agents.

DESCRIPTION AND THE PREFERRED EMBODIMENTS

The present invention relates to novel 5-substituted-2(1H)-pyridone compounds. This invention also describes the non-toxic pharmaceutically acceptable salts; the method of preparing these compounds; and their pharmaceutical uses.

The novel compounds of this invention are described by the structural Formula I:

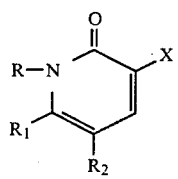

(I)

wherein X represents hydrogen, alkyl, cyano, halogen, trifluoromethyl, alkoxy, hydroxy, hydroxy lower alkyl, amino, alkylamino, dialkylamino, acylamino, ureido, guanidino, carbamylguanidino, cyanoguanidino, and thioureido; R represents hydrogen, lower alkyl, or hydroxyloweralkyl; $R_1$ represents hydrogen or lower alkyl; $R_2$ represents a nitrogen containing heterocyclic ring such as pyrimidinyl, pyridazinyl or pyrazinyl, which rings may optionally be substituted by one or more lower alkyl, hydroxyloweralkyl, hydroxyl, alkoxy, alkanoyl, amino, alkylamino or dialkylamino, some of which compounds exist in tautomeric form.

More specifically, the chemical compounds of this invention which have particular usefulness as cardiotonic agents and whose properties are preferred are described by the Formulae II to VI.

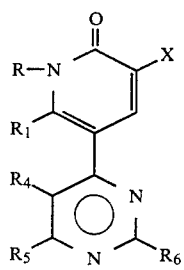

(II)

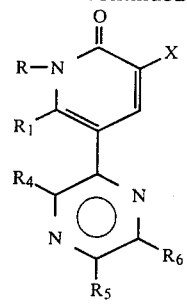

(III)

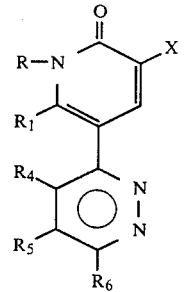

(IV)

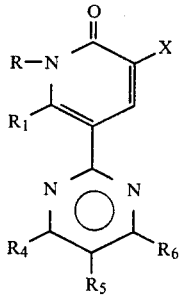

(V)

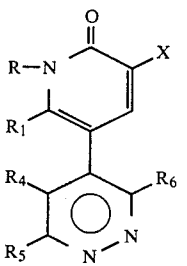

(VI)

wherein X, R, $R_1$, and $R_2$ are hereinbefore described, and each of $R_4$, $R_5$ and $R_6$ represent hydrogen, halogen, trifluoromethyl, loweralkyl, hydroxyloweralkyl, hydroxy, alkoxy, alkanoyl, amino, alkylamino and dialkylamino.

In the descriptive portions of this invention the following definitions apply:

"alkyl" refers to a loweralkyl hydrocarbon group containing from 1 to about 7 carbon atoms which may be straight, chained or branched.

"acyl" refers to any organic radical derived from an organic acid having up to 12 carbon atoms by the removal of its hydroxyl group such as formyl, acetyl, propionyl, 3-carboxy-2-propenol, camphoryl, benzoyl, toluoyl or heteroyl such as pyridinoyl, piperidinyl, thienoyl, etc.

"alkanoyl" refers to these acyl derivatives of a hydroxy-containing compound therein.

"alkoxy" refers to a lower alkoxy group containing from 1 to about 6 carbon atoms which may be straight chained or branched.

The compounds of this invention are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention it is convenient to form the free base form; however, appropriate pharmaceutically-acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are useful as sources of the free base form even if the particular salts per se is desired only as an intermediate product as for example when the salt is formed only for purposes of purification and identification, or when it is used as an intermediate in preparing a pharmaceutically-acceptable salt by ion exchange procedures.

The compounds of this invention may be prepared by the following general procedure:

One process aspect of the invention resides in reacting either α-hetero-β-(R'R"N) acrolein or α-hetero-malonaldehyde with α-cyanoactamide to produce 1,2-dihydro-2-oxo-5-hetero-nicotinonitrile and then partially hydrolyzing the 1,2-hydro-2-oxo-5-hetero-nicotinonitrile to produce 1,2-dihydro-2-oxo-5-hetero-nicotinamide where hetero is defined as a nitrogen containing heterocyclic compound as previously described.

In another process aspect, the invention resides in producing 3-amino-5-hetero-2(1H)-pyridone by the steps comprising first heating 1,2-dihydro-2-oxo-5-hetero-nicotinic acid with a mixture of concentrated sulfuric acid and concentrated nitric acid to produce 3-nitro-5-hetero-2(1H)-pyridone.

The above process aspects of the invention are illustrated by the following flow sheet which also shows the conversion of 1,2-dihydro-2-oxo-5-hetero-nicotinonitrile to 1,2-dihydro-2-oxo-5-hetero-nicotinic acid by hydrolysis with aqueous sulfuric acid:

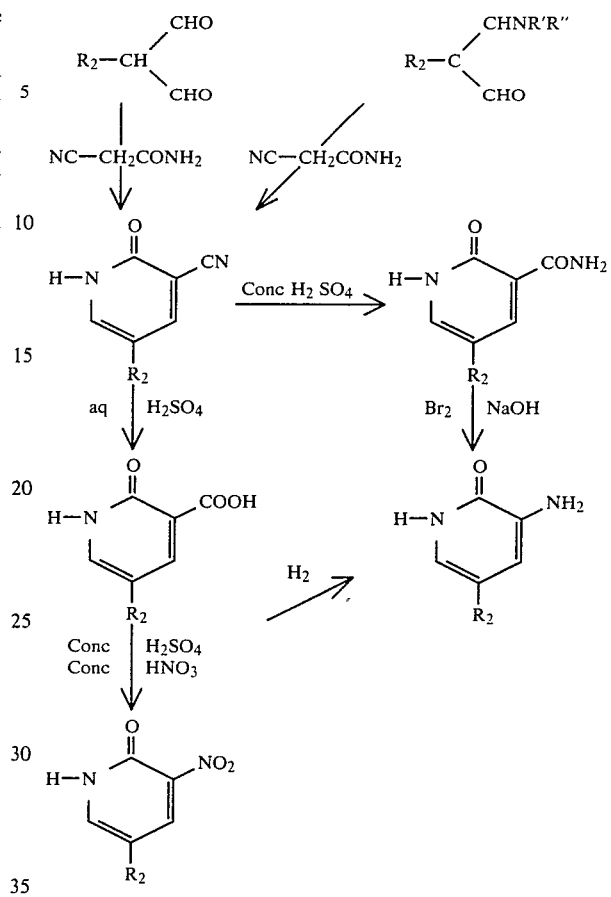

Alternatively, 1,2-dihydro-2-oxo-5-hetero-nicotinonitrile is converted to 3-nitro-5-hetero-2(1H)-via 5-hetero-2(1H) pyridone by first refluxing 1,2-dihydro-2-oxo-5-hetero-nicotinonitrile with aqueous sulfuric acid to produce 1,2-dihydro-2-oxo-5-heteronicotinic. acid and then refluxing in quinoline to produce 5-hetero-2(1H)-pyridone, which may then be heated with a mixture of concentrated sulfuric acid and concentrated nitric acid to produce 3-nitro-5-hetero-2(1H)-pyridone.

Appropriately desired end products having various X, $R_4$, $R_5$ and $R_6$ substituents can be prepared at a suitable stage of the synthesis by using suitable reactions in order to convert one group to another.

Thus, for example, a nitro group may be hydrogenated to the corresponding amine. This may then be mono- or di-alkylated with loweralkyl halides or sulfates. It may also be reacted by diazotization to the diazonium fluoroborate which is then thermally decomposed to the fluoride. The amine may also be diazotized and heated in water or an alcohol to form the hydroxy or desired alkoxy group. Diazotization may also be carried out followed by a Sandmeyer type reaction to yield the halo groups of chloro, bromo or iodo. Diazotization followed by addition of cuprous cyanide results in the cyano compound. A halo compound such as the chloro, bromo or iodo may be reacted with trifluoromethyliodide and copper powder at about 150° C. in dimethylformamide to obtain the trifluoromethyl compound.

The amine compounds may be reacted with O-phenyl-N-cyanoisourea to form the corresponding cyanoguanidine compound. This condensation can be carried out in an inert solvent at elevated temperatures. Alternatively, the condensation reaction can be carried out with sodium dicyanamide.

Hydrolysis of the cyanoquanidine with an aqueous mineral acid results in the formation of the corresponding carbamylguanidine.

Other guanidine compounds may be prepared by converting the amines by reaction with the acid-addition salt of an S-alkyl-isothiourea, such as an S-methylisothiourea.

The amine compounds may be reacted with acylating agents such as acid chlorides, anhydrides, or esters to form the corresponding acylamine compounds.

The amine compounds may be reacted with isocyanates or isothiocyanates to form the corresponding ureido or thioureido compounds.

The compounds of Formula I which may exist in tautomeric form are considered within the scope of this invention.

The starting materials of this invention are either known compounds or their method of preparation is by conventional methods as described in U.S. Pat. No. 4,004,012 of Lesher et al.

For all these purposes, the compounds of this invention can be normally administered orally or parenterally. The term "parenteral" as used herein, includes subcutaneous injection, intravenous, intramuscular or intrasternal injection or infusion techniques.

The pharmaceutical compositions may be in the form of a tablet, capsule, elixir, suspension or the like or as a sterile injectable preparation, for example, as a sterile injectable aqueous suspension. This suspension may be formulated according to the known art using suitable dispersing or wetting agents and suspending agents. The sterile injectable preparation may also be a sterile injectable solution or suspension in a non-toxic parenterally acceptable diluent or solvent, for example, as an aqueous solution buffered to a pH of 4.0 to 7.0 and made isotonic with sodium chloride.

Further, these compounds may be formulated so that for every 100 parts by weight of the compositions, there are present between 5 and 95 parts by weight of the active ingredient. The dosage unit form will generally contain between about 1 mg and about 500 mg of the active ingredients of this invention. The preferred unit dose is between about 10 mg and about 100 mg.

The dosage regimen in carrying out the methods of this invention is that which insures maximum therapeutic response until improvement is obtained and thereafter the minimum effective level which gives relief. Thus, in general, the dosages are those that are therapeutically effective for cardiotonic activity. In general, the daily dose can be between about 0.5 mg/kg and 70 mg/kg (preferably in the range of 2-25 mg/kg/day), bearing in mind, of course, that in selecting the appropriate dosage in any specific case, consideration must be given to the patient's weight, general health, age, and other factors which may influence response to the drug.

The usefulness of the compound of Formula I, or pharmaceutically-acceptable acid-addition salt thereof, as a cardiotonic agent is demonstrated by its effectiveness in standard pharmacological test procedures, for example, in causing a significant increase in the contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the above-noted isolated catatria and papillary muscle procedure, the compounds of Formula I or pharmaceutically-acceptable acid-addition salt thereof at doses of 10, 30, 100 and 300 g./ml. were found to cause significant increases, that is about 25% or greater, e.g., up to about 150 to 200%, in papillary muscle force and significant increases, that is, about 25% or greater, e.g., up to about 50 to 200%, in right atrial force, while causing only a low percentage increase (about one-half of less than the percentage increase in right atrial force or papillary muscle force) in right atrial rate.

Similarly, when tested by the above-noted anesthetized dog procedure, the compounds of Formula I or pharmaceutically-acceptable acid-addition salt thereof at doses of about 1.0, 3.0 and 10.0 mg/kg administered intravenously were found to cause significant increases, that is, about 25% or greater, in cardiac contractile force or cardiac contractility with lower changes in heart rate and blood pressure.

The following are detailed Examples which show the preparations of the compounds of this invention. They are to be construed as illustrations of said compounds and not as limitations thereof.

EXAMPLE I

Preparation of α-(4-pyrimidinyl)-β-dimethylaminoacrolein.

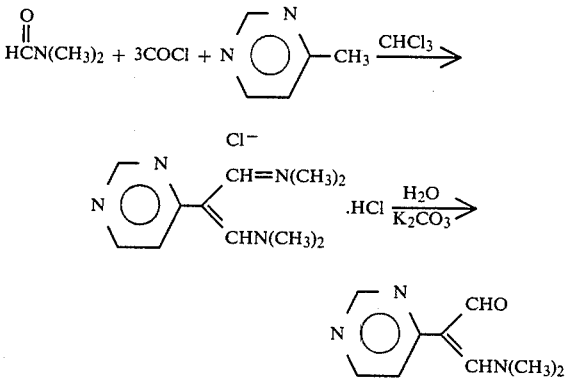

A. Into a tared 2 liter Erlenmeyer flask, containing 1 liter of chloroform being stirred magnetically and being chilled in an ice bath, was bubbled phosgene. The flask was weighed periodically and bubbling stopped when 324 g of phosgene had been added. Meanwhile, a 5 liter 3-necked flask was charged with 700 ml of chloroform and 620 ml of dimethylformamide (DMF). The flask was fitted with a thermometer and a mechanical stirrer and was chilled in a methanol ice bath to −5° C. The final mixture was stirred for 15 minutes before a solution of 98.1 g of methyl pyrimidine in 50 ml of chloroform was added dropwise over 25 minutes at a temperature of 0° C. The reaction mixture was stirred at 0° C. for 15 minutes and then the reaction mixture was allowed to warm to room temperature. A heating mantle was placed around the flask and the reaction mixture was heated. At 54° C. a solid began to precipitate out of the reaction mixture and the mixture was refluxed for one hour.

The reaction mixture was then cooled in an ice bath before being filtered and the solid was washed with 500 ml of chloroform. The solid was dried under high vacuum at 70° C. for 3½ hours to give the product as a light yellow solid.

B. Ten gram portions of the solid from Part A were dissolved in 110 ml of distilled water and then chilled in an ice bath. Anhydrous potassium carbonate was added slowly to the solution and when neutralization had been completed an additional 5 g of anhydrous potassium carbonate was added. Then 110 ml of chloroform was added to the solution and left to stir overnight.

The reaction mixture was then extracted with chloroform, dried over sodium sulfate and the chloroform was removed in vacuo. The residue crystallized to yield-α-(4-pyrimidinyl)-β-dimethylaminoacrolein.

EXAMPLE II

Preparation of α-(2-pyrazinyl)-β-dimethyl aminoacrolein.

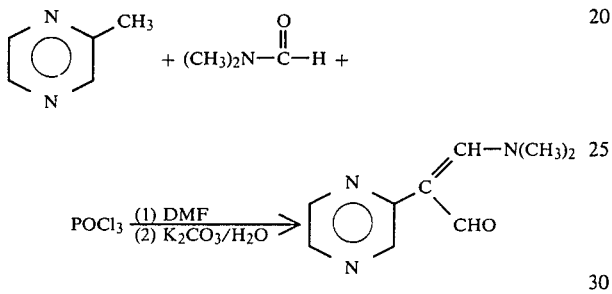

525 ml of dimethylformamide was cooled in an ice bath in a 2 liter flask equipped with magnetic stirrer, thermometer, addition funnel and drying tube to 4° C. To this was then added 244 g of phosphorous oxychloride over a period of 1 hour 20 minutes while maintaining a temperature of less than 10° C. The mixture was stirred for an additional 30 minutes. To this was then added 50.0 g 2-methylpyrazine over a period of 30 minutes while maintaining the temperature at 8°-11° C. The ice bath was removed and the solution was heated to 80° C. The heating was stopped and the mixture cooled to 70° C. in a water bath. Heating was resumed to maintain a temperature of 70° C. which was maintained for a total of 5 hours. The mixture was allowed to stand at room temperature overnight.

After cooling in ice bath, with mechanical stirring, the mixture was poured into 1500 ml H₂O/1.5 kg K₂CO₃ over a period of 30 minutes. To this was then added 80 ml of ethanol/200 ml of toluene. The mixture was stirred for 1 hour. A large amount of precipitated salts was removed by filtration and rinsed with 500 ml ethanol. The lower layer was separated and extracted with 500 ml of EtOH/200 ml toluene. The upper layers were combined. This solution was then evaporated in vacuo at 45°-50° C.

A dark oil residue which formed was then evaporated at 50°-60° C./0.05 mm. This gave a dark brown solid. The solid was transferred to a 2-1 Erlenmeyer by breaking up in 500 ml hot isopropyl acetate. Another 500 ml of isopropyl acetate was added and the slurry heated, with stirring and low boiling for 30 minutes. This was then filtered hot and the filtrate allowed to cool with stirring.

The slurry was then cooled with stirring in an ice bath for 45 minutes, filtered and the solid washed with isopropyl acetate. This solid was dissolved in 500 ml boiling isopropyl acetate and filtered hot. The solution was cooled in an ice bath for ½ hour and filtered to yield α-(2-pyrazinyl)-β-dimethylaminoacrolein mp. 103°-104° C.

Similarly, when the procedures of Examples I or II are followed and the related methylated heterocyclic compound are utilized, the compounds below may be prepared:

α-(2-methyl-4-pyrimidinyl)-β-dimethylamino acrolein

α-(2,5-dimethyl-4-pyrimidinyl)-β-dimethylamino acrolein

α-(2,6-dimethyl-4-pyrimidinyl)-β-dimethylamino acrolein

α-(2-hydroxy-4-pyrimidinyl)-β-dimethylamino acrolein

α-(2-methoxy-4-pyrimidinyl)-β-dimethylamino acrolein

α-(2,6-dimethoxy-4-pyrimidinyl)-β-dimethylamino acrolein

α-(2-hydroxymethyl-4-pyrimidinyl)-β-dimethylamino acrolein

α-(2-amino-4-pyrimidinyl)-β-dimethylamino acrolein

α-(2-methylamino-4-pyrimidinyl)-β-dimethylamino acrolein

α-(6-methyl-2-pyrazinyl)-β-dimethylamino acrolein

α-(3,6-dimethyl-2-pyrazinyl)-β-dimethylamino acrolein

α-(3-methyl-2-pyrazinyl)-β-dimethylamino acrolein

α-(6-hydroxy-2-pyrazinyl)-β-dimethylamino acrolein

α-(6-methoxy-2-pyrazinyl)-β-dimethylamino acrolein

α-(3,6-dimethoxy-2-pyrazinyl)-β-dimethylamino acrolein

α-(3-methoxy-2-pyrazinyl)-β-dimethylamino acrolein

α-(6-hydroxymethyl-2-pyrazinyl)-β-dimethylamino acrolein

α-(6-amino-2-pyrazinyl)-β-dimethylamino acrolein

α-(6-methylamino-2-pyrazinyl)-β-dimethylamino acrolein

α-(3-pyridazinyl)-β-dimethylamino acrolein

α-(4-methyl-3-pyridazinyl)-β-dimethylamino acrolein

α-(6-methyl-3-pyridazinyl)-β-dimethylamino acrolein

α-(6-hydroxy-3-pyridazinyl)-β-dimethylamino acrolein

α-(6-methoxy-3-pyridazinyl)-β-dimethylamino acrolein

α-(6-amino-3-pyridazinyl)-β-dimethylamino acrolein

α-(4,6-dimethoxy-3-pyridazinyl)-β-dimethylamino acrolein

EXAMPLE III

Preparation of 2-oxo-5-(4-pyrimidinyl)nicotinonitrile

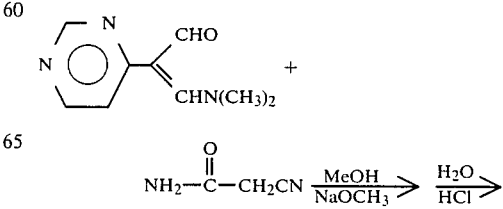

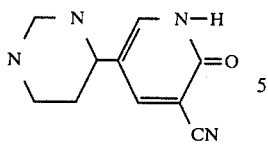

In a 1-liter, 3-necked flask 49.8 g of α-(4-pyrimidinyl)-β-dimethylamino acrolein and 33.6 g of 2-cyanoacetamide were dissolved in 450 l of methanol under a nitrogen atmosphere. After total dissolution, 27 g of sodium methoxide in 200 ml of methanol was added. The reaction mixture was heated to reflux and kept there for 5 minutes and then allowed to cool and filtered. The solid was washed with cold methanol then ether and partially air dried. The solid was then dissolved in 2-liter of distilled water and filtered to remove a small amount of undissolved impurity. The filtrate was then acidified to a pH of 6 by addition of 6N HCl. This caused a large amount of solid to precipitate out. The solid was filtered, washed with water and dried to obtain 2-oxo-5-(4-pyrimidinyl)nicotinonitrile.

EXAMPLE IV

Preparation of
1,2-dihydro-2-oxo-5-(2-pyrazinyl)nicotinonitrile

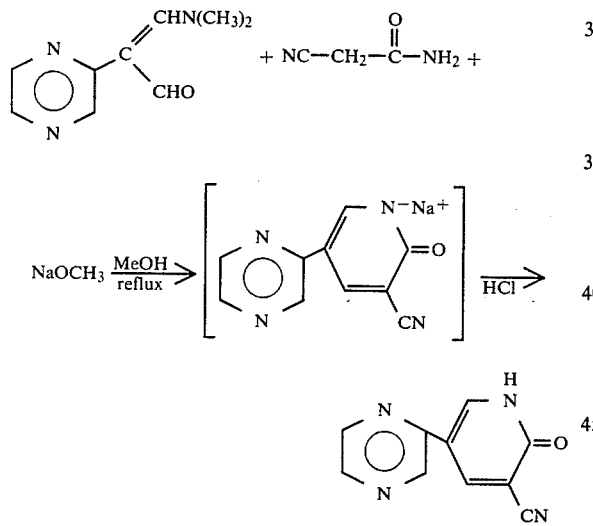

26.6 g of α-(2-pyrazinyl)-β-dimethylamino acrolein and 12.7 g of 2-cyanoacetamide were dissolved together in 400 ml methanol in a 1 liter flask equipped with a condenser and mechanical stirrer. To this was then added 16.3 g sodium methoxide and the mixture was heated to reflux. The mixture was refluxed for 1 hour, during which time a thick slurry formed. The mixture was then allowed to cool with stirring and filtered. The solid was washed with methanol and dried yielding a slightly moist, pale green solid. The solid was dissolved in 1250 ml of water and filtered. The solution was adjusted to pH 4–6 with 6N HCl yielding a thick precipitation. The slurry was stirred in an ice bath for 30 minutes. The slurry was then filtered and the solid was washed with 200 ml water, 200 ml isopropyl alcohol and 200 ml of ether to yield a beige solid, m.p. 250° C., which was 1,2-dihydro-2-oxo-5-(2-pyrazinyl)-nicotinonitrile.

Similarly, when the procedures of Example III or IV are followed and the related acrolein compounds are utilized, the compounds below may be prepared:

2-oxo-5-(2-methyl-4-pyrimidinyl)nicotinonitrile
2-oxo-5-(2,5-dimethyl-4-pyrimidinyl)nicotinonitrile
2-oxo-5-(2,6-dimethyl-4-pyrimidinyl)nicotinonitrile
2-oxo-5-(2-hydroxy-4-pyrimidinyl)nicotinonitrile
2-oxo-5-(2-methoxy-4-pyrimidinyl)nicotinonitrile
2-oxo-5-(2,6-dimethoxy-4-pyrimidinyl)nicotinonitrile
2-oxo-5-(2-hydroxymethyl-4-pyrimindinyl)-nicotinonitrile
2-oxo-5-(2-amino-4-pyrimidinyl)nicotinonitrile
2-oxo-5-(2-methylamino-4-pyrimidinyl)nicotinonitrile
2-oxo-5-(6-methyl-2-pyrazinyl)nicotinonitrile
2-oxo-5-(3,6-dimethyl-2-pyrazinyl)nicotinonitrile
2-oxo-5-(3-methyl-2-pyrazinyl)nicotinonitrile
2-oxo-5-(6-hydroxy-2-pyrazinyl)nicotinonitrile
2-oxo-5-(6-methoxy-2-pyrazinyl)nicotinonitrile
2-oxo-5-(3,6-dimethoxy-2-pyrazinyl)nicotinonitrile
2-oxo-5-(3-methoxy-2-pyrazinyl)nicotinonitrile
2-oxo-5-(6-hydroxymethyl-2-pyrazinyl)nicotinonitrile
2-oxo-5-(6-amino-2-pyrazinyl)nicotinonitrile
2-oxo-5-(6-methylamino-2-pyrazinyl)nicotinonitrile
2-oxo-5-(3-pyridazinyl)nicotinonitrile
2-oxo-5-(4-methyl-3-pyridazinyl)nicotinonitrile
2-oxo-5-(6-methyl-3-pyridazinyl)nicotinonitrile
2-oxo-5-(6-hydroxy-3-pyridazinyl)nicotinonitrile
2-oxo-5-(6-methoxy-3-pyridazinyl)nicotinonitrile
2-oxo-5-(6-amino-3-pyridazinyl)nicotinonitrile
2-oxo-5-(4,6-dimethoxy-3-pyridazinyl)nicotinonitrile

EXAMPLE V

Preparation of
1,2-dihydro-2-oxo-5-(2-pyrazinyl)nicotinamide

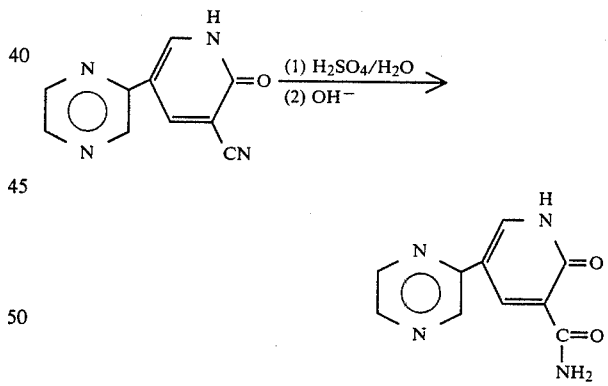

25.0 g of 1,2-dihydro-2-oxo-5-(2-pyrazinyl)-nicotinonitrile was dissolved in a solution of 228 ml concentrated sulfuric acid and 16 ml water. This gave a dark red-orange solution which was heated on a steam bath for 2 hours and then allowed to cool. The mixture was then poured on to about 1.5 kg crushed ice with mechanical stirring while cooling in an ice bath. The mixture was brought to pH 5 with a solution of 342 g NaOH in 1 liter of water. The mixture was stirred in an ice bath for 15 minutes, filtered and the solid washed with 300 ml of water. The solid was ground with a mortar and pestle and dissolved in 1500 ml boiling dimethylformamide. This was filtered hot and cooled to yield a light beige fluffy solid which was 1,2-dihydro-2-oxo-5-(2-pyrazinyl)nicotinamide.

EXAMPLE VI

Preparation of 2-oxo-5-(4-pyrimidinyl)-nicotinamide

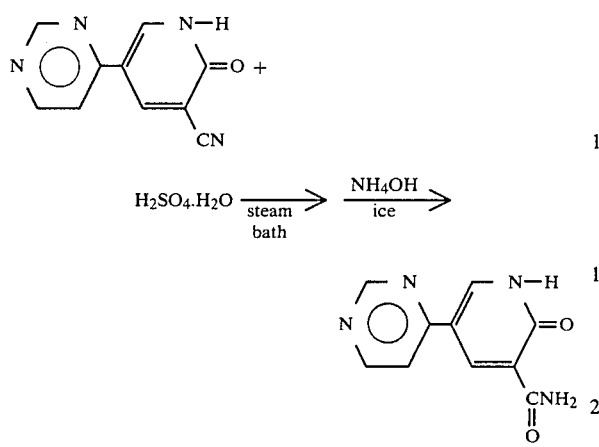

In a 500-ml Erlenmeyer flask 23.0 g of 2-oxo-5-(4-pyrimidinyl)nicotinonitrile was dissolved in 194.3 g of dilute H₂SO₄. The solution was heated on the steam bath with occasional swirling for 2½ hours. It was then poured into a slurry of 225 ml of concentrated ammonia and 610 g of ice. A white solid precipitated out and was filtered, washed with distilled water and then isopropanol. The white solid was dried overnight at 100° C. and yielded 2-oxo-5-(4-pyrimidinyl)nicotinamide.

Similarly, when the procedures of Example V or VI are followed and the related nicotinonitrile compounds are utilized, the compounds below may be prepared:
2-oxo-5-(2-methyl-4-pyrimidinyl)nicotinamide
2-oxo-5-(2,5-dimethyl-4-pyrimidinyl)nicotinamide
2-oxo-5-(2,6-dimethyl-4-pyrimidinyl)nicotinamide
2-oxo-5-(2-hydroxy-4-pyrimidinyl)nicotinamide
2-oxo-5-(2-methoxy-4-pyrimidinyl)nicotinamide
2-oxo-5-(2,6-dimethoxy-4-pyrimidinyl)nicotinamide
2-oxo-5-(2-hydroxymethyl-4-pyrimidinyl)nicotinamide
2-oxo-5-(2-amino-4-pyrimidinyl)nicotinamide
2-oxo-5-(2-methylamino-4-pyrimidinyl)nicotinamide
1,2-dihydro-2-oxo-5-(6-methyl-2-pyrazinyl)nicotinamide
1,2-dihydro-2-oxo-5-(3,6-dimethyl-2-pyrazinyl)-nicotinamide
1,2-dihydro-2-oxo-5-(3-methyl-2-pyrazinyl)nicotinamide
1,2-dihydro-2-oxo-5-(6-hydroxy-2-pyrazinyl)-nicotinamide
1,2-dihydro-2-oxo-5-(6-methoxy-2-pyrazinyl)-nicotinamide
1,2-dihydro-2-oxo-5-(3,6-dimethoxy-2-pyrazinyl)-nicotinamide
1,2-dihydro-2-oxo-5-(3-methoxy-2-pyrazinyl)-nicotinamide
1,2-dihydro-2-oxo-5-(6-hydroxymethyl-2-pyrazinyl)-nicotinamide
1,2-dihydro-2-oxo-5-(6-amino-2-pyrazinyl)nicotinamide
1,2-dihydro-2-oxo-5-(6-methylamino-2-pyrazinyl)-nicotinamide
1,2-dihydro-2-oxo-5-(3-pyridazinyl)nicotinamide
1,2-dihydro-2-oxo-5-(4-methyl-3-pyridazinyl)-nicotinamide
1,2-dihydro-2-oxo-5-(6-methyl-3-pyridazinyl)-nicotinamide
1,2-dihydro-2-oxo-5-(6-hydroxy-3-pyridazinyl)-nicotinamide
1,2-dihydro-2-oxo-5-(6-methoxy-3-pyridazinyl)-nicotinamide
1,2-dihydro-2-oxo-5-(6-amino-3-pyridazinyl)nicotinamide
1,2-dihydro-2-oxo-5-(4,6-dimethoxy-3-pyridazinyl)-nicotinamide

EXAMPLE VII

Preparation of 3-amino-5-(4-pyrimidyl)-2-(1H)-pyridone

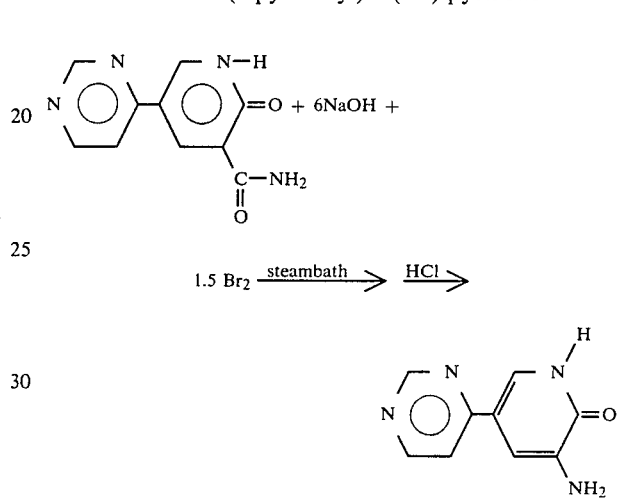

In a 500-ml Erlenmeyer flask 11.1 g of sodium hydroxide was dissolved in 50 ml of water. Ice was then added to bring the volume to 200 ml. Then 3.56 ml of bromine was added and stirred until dissolution. 10 g of 2-oxo-5-(4-pyrimidinyl)nicotinamide was then added quickly with vigorous stirring and then transferred to a steam bath. Heating and stirring were continued for four hours and ten minutes and then the reaction mixture was cooled in an ice bath before being acidified by addition of 6N HCl. Stirring was continued for 30 minutes during which time a solid precipitated out slowly. Saturated NaHCO₃ solution was added to bring the pH to 8. This caused the solid to turn from orange to tan in color. The solid was filtered and washed with water, then isopropanol. The solid was dried overnight under house vacuum at 100° C. The dried solid was shown to be the desired 3-amino-5-(4-pyrimidyl)-2(1H)-pyridone.

EXAMPLE VIII

Preparation of 3-amino-5-(2-pyrazinyl)-2(1H)pyridone methane sulfonate

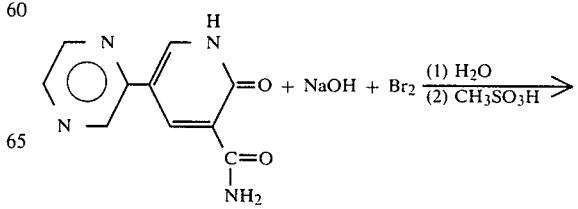

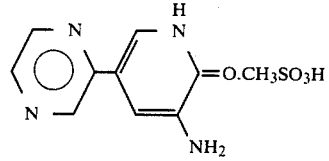

22.1 g sodium hydroxide was dissolved in 310 ml of water. This was cooled to −1° C. in an ice/MeOH bath. To this was added 5.6 ml bromine over a period of 20 minutes maintaining a temperature of −1° C. After addition was completed and all bromine dissolved, 19.6 g of 1,2-dihydro-2-oxo-5-(2-pyrazinyl)nicotinamide was added and the mixture heated on a steam bath, with occasional swirling, for 3 hours. The mixture was allowed to cool, and then 85 ml 6N HCl was added over a period of 10 minutes. The mixture was then adjusted to pH 8 with saturated Na HCO₃ solution to yield a precipitate. The mixture was stirred at room temperature for 15 minutes, then in ice bath for 30 minutes, and filtered. The solid was washed with 150 ml water, 100 ml isopropanol, 100 ml ether and then dried.

This gave 14.3 g of a light green powder. 14.0 g of the powder was suspended in 150 ml methanol. To this was added 8.0 g methanesulfonic acid and a solid precipitated. The solid was filtered and washed with methanol, then ether, and dried to yield a light orange powder which was 3-amino-5-(2-pyrazinyl)-2(1H)pyridone methane sulfonate, m.p. 243°–246° C. (dec).

Similarly, when the procedures of Example VII or VIII are followed and the related nicotinamide compounds are utilized there may be obtained compounds which include the following:

3-amino-5-(2-methyl-4-pyrimidinyl)-2(1H)-pyridone
3-amino-5-(2,5-dimethyl-4-pyrimidinyl)-2(1H)-pyridone
3-amino-5-(2,6-dimethyl-4-pyrimidinyl)-2(1H)-pyridone
3-amino-5-(2-hydroxy-4-pyrimidinyl)-2(1H)-pyridone
3-amino-5-(2-methoxy-4-pyrimidinyl)-2(1H)-pyridone
3-amino-5-(2,6-dimethoxy-4-pyrimidinyl)-2(1H)-pyridone
3-amino-5-(2-hydroxymethyl-4-pyrimidinyl)-2(1H)-pyridone
3-amino-5-(2-amino-4-pyrimidinyl)-2(1H)-pyridone
3-amino-5-(2-methylamino-4-pyrimidinyl)-2(1H)-pyridone
3-amino-5-(6-methyl-2-pyrazinyl)-2(1H)-pyridone
3-amino-5-(3,6-dimethyl-2-pyrazinyl)-2(1H)-pyridone
3-amino-5-(3-methyl-2-pyrazinyl)-2(1H)-pyridone
3-amino-5-(6-hydroxy-2-pyrazinyl)-2(1H)-pyridone
3-amino-5-(6-methoxy-2-pyrazinyl)-2(1H)-pyridone
3-amino-5-(3,6-dimethoxy-2-pyrazinyl)-2(1H)-pyridone
3-amino-5-(3-methoxy-2-pyrazinyl)-2(1H)-pyridone
3-amino-5-(6-hydroxymethyl)-2-pyrazinyl)-2(1H)-pyridone
3-amino-5-(6-amino-2-pyrazinyl)-2(1H)-pyridone
3-amino-5-(6-methylamino-2-pyrazinyl)-2(1H)-pyridone
3-amino-5-(3-pyridazinyl)-2(1H)-pyridone
3-amino-5-(4-methyl-3-pyridazinyl)-2(1H)-pyridone
3-amino-5-(6-methyl-3-pyridazinyl)-2(1H)-pyridone
3-amino-5-(6-hydroxy-3-pyridazinyl)-2(1H)-pyridone
3-amino-5-(6-methoxy-3-pyridazinyl)-2(1H)-pyridone
3-amino-5-(6-amino-3-pyridazinyl)-2(1H)-pyridone
3-amino-5-(4,6-dimethoxy-3-pyridazinyl)-2(1H)-pyridone If desired, any of the above mentioned compounds may be treated with an alkylating agent of the formula R-An wherein R is as hereinbefore described and An is an anion of a strong inorganic acid or an organic sulfonic acid to form the N-substituted derivative.

EXAMPLE IX

Preparation of 5-(4-pyrimidyl)-2-(1H)pyridone:

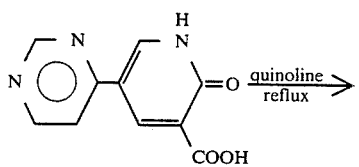

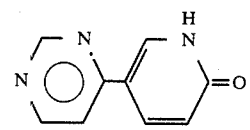

90.8 g of 2-oxo-5-(4-pyrimidinyl)nicotinic acid was mixed with 900 ml of quinoline and then heated to reflux overnight. The mixture was then cooled and poured into 1800 ml of anhydrous ether. The mixture was stirred for 30 minutes, filtered and the solid was washed with 2 liters of ether. The solid was dried, recrystallized in 100 ml of hot dimethylformamide and dried to yield 5-(4-pyrimidyl)-2(1H)pyridone m.p. 250° C.

Similarly, when following the procedures of Example IX and utilizing the related nicotinic acid, there may be obtained the following compounds:

5-(2-methyl-4-pyrimidinyl)-2(1H)-pyridone
5-(2,5-dimethyl-4-pyrimidinyl)-2(1H)-pyridone
5-(2,6-dimethyl-4-pyrimidinyl)-2(1H)-pyridone
5-(2-hydroxy-4-pyrimidinyl)-2(1H)-pyridone
5-(2-methoxy-4-pyrimidinyl)-2(1H)-pyridone
5-(2,6-dimethoxy-4-pyrimidinyl)-2(1H)-pyridone
5-(2-hydroxymethyl-4-pyrimidinyl)-2(1H)-pyridone
5-(2-amino-4-pyrimidinyl)-2(1H)-pyridone
5-(2-methylamino-4-pyrimidinyl)-2(1H)-pyridone
5-(6-methyl-2-pyrazinyl)-2(1H)-pyridone
5-(3,6-dimethyl-2-pyrazinyl)-2(1H)-pyridone
5-(3-methyl-2-pyrazinyl)-2(1H)-pyridone
5-(6-hydroxy-2-pyrazinyl)-2(1H)-pyridone
5-(6-methoxy-2-pyrazinyl)-2(1H)-pyridone
5-(3,6-dimethoxy-2-pyrazinyl)-2(1H)-pyridone
5-(3-methoxy-2-pyrazinyl)-2(1H)-pyridone
5-(6-hydroxymethyl-2-pyrazinyl)-2(1H)-pyridone
5-(6-amino-2-pyrazinyl)-2(1H)-pyridone
5-(6-methylamino-2-pyrazinyl)-2(1H)-pyridone
5-(3-pyridazinyl)-2(1H)-pyridone
5-(4-methyl-3-pyridazinyl)-2(1H)-pyridone
5-(6-methyl-3-pyridazinyl)-2(1H)-pyridone
5-(6-hydroxy-3-pyridazinyl)-2(1H)-pyridone
5-(6-methoxy-2-pyridazinyl)-2(1H)-pyridone
5-(6-amino-3-pyridazinyl)-2(1H)-pyridone
5-(4,6-dimethoxy-3-pyridazinyl)-2(1H)-pyridone If desired, any of the above mentioned compounds may be treated with an alkylating agent of the formula R-An wherein R is as hereinbefore described and An is an anion of a strong inorganic acid or an organic sulfonic acid to form the N-substituted derivative.

The compounds of Examples VII–IX may be prepared into suitable formulations following a procedure as described in "Remington's Pharmaceutical Sciences", F. W. Martin et al, 14th Ed., MACK Publishing Co., Easton, Pa. (1965).

I claim:

1. A compound having the formula:

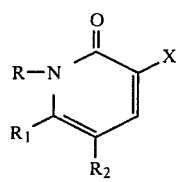

wherein X is selected from the group consisting of hydrogen, alkyl, cyano, halogen, trifluoromethyl, alkoxy, hydroxy, hydroxyloweralkyl, amino, alkylamino, dialkylamino, acylamino, ureido, guanidino, carbamylguanidino, cyanoguanidine or thioureido; R is selected from the group consisting of hydrogen, loweralkyl or hydroxyloweralkyl; $R_1$ is selected from the group consisting of hydrogen or loweralkyl; $R_2$ is a nitrogen containing heterocyclic ring selected from the group consisting of pyrimidinyl, pyridazinyl, pyrazinyl, or a pyrimidinyl, pyridazinyl or pyrazinyl having one or more substituents selected from the group consisting of loweralkyl, hydroxyloweralkyl, hydroxyl, alkoxy, alkanoyl, amino, alkylamino or dialkylamino, and the pharmaceutically acceptable salts thereof.

2. A compound according to claim 1, which is 3-amino-5-(2-pyrazinyl)-2(1H)-pyridone and the salts thereof.

3. A compound according to claim 1, which is 3-amino-5-(4-pyrimidyl)-2(1H)-pyridone and the salts thereof.

4. A method for increasing cardiac contractility in mammals requiring such treatment which comprises administering to such mammal an effective amount of a cardiotonic of the formula:

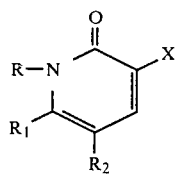

wherein X is selected from the group consisting of hydrogen, alkyl, cyano, halogen, trifluoromethyl, alkoxy, hydroxy, hydroxyloweralkyl, amino, alkylamino, dialkylamino, acylamino, ureido, guanidino, carbamylamidino, cyanoguanidino or thioureido; $R_1$ is selected from the group consisting of hydrogen, loweralkyl or hydroxyloweralkyl; $R_2$ is selected from the group consisting of hydrogen or loweralkyl; $R_3$ is a nitrogen containing heterocyclic ring selected from the group consisting of pyrimidinyl, pyridazinyl, pyrazinyl, or a pyrimidinyl, pyridazinyl or pyrazinyl having one or more substituents selected from the group consisting of loweralkyl, hydroxyloweralkyl, hydroxyl, alkoxy, alkanoyl, amino, alkylamino or dialkylamino, and the pharmaceutically acceptable salts thereof.

5. The method according to claim 4, wherein said compound is
5-(4-pyrimidyl)-2(1H)-pyridone and the salts thereof.

6. The method according to claim 4, wherein said compound is
3-amino-5-(2-pyrazinyl)-2(1H)-pyridone and the salts thereof.

7. The method according to claim 4, wherein said compound is
3-amino-5-(4-pyrimidyl)-2(1H)-pyridone and the salts thereof.

8. A cardiotonic composition for increasing cardiac contractility in mammals, said composition comprising a pharmaceutically acceptable carrier and an effective amount of an active cardiotonic compound of the formula.

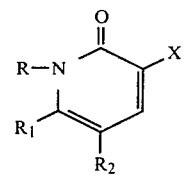

wherein X is selected from the group consisting of hydrogen, alkyl, cyano, halogen, trifluoromethyl, alkoxy, hydroxy, hydroxyloweralkyl, amino, alkylamino, dialkylamino, acylamino, ureido, guanidino, carbamylamidino, cyanoguanidino or thioureido; R is selected from the group consisting of hydrogen, loweralkyl or hydroxyloweralkyl; $R_1$ is selected from the group consisting of hydrogen or loweralkyl; $R_2$ is nitrogen containing heterocyclic ring selected from the group consisting of pyrimidinyl, pyridazinyl, pyrazinyl, or a pyrimidinyl, pyridazinyl or pyrazinyl having one or more substituents selected from the group consisting of loweralkyl, hydroxyloweralkyl, hydroxyl, alkoxy, alkanoyl, amino, alkylamino or dialkylamino, and the pharmaceutically acceptable salts thereof.

9. A composition according to claim 8, wherein said active compound is:
5-(4-pyrimidyl)-2(1H)-pyridone and the salts thereof.

10. A composition according to claim 8, wherein said active compound is:
3-amino-5-(2-pyrazinyl)-2(1H)-pyridone and the salts thereof.

11. A composition according to claim 8, wherein said active compound is:
3-amino-5-(4-pyrimidyl)-2(1H)-pyridone and the salts thereof.

* * * * *

UNITED STATES PATENT AND TRADEMARK OFFICE
CERTIFICATE OF CORRECTION

PATENT NO. : 4,514,400
DATED : April 30, 1985
INVENTOR(S) : Henry F. Campbell

It is certified that error appears in the above-identified patent and that said Letters Patent is hereby corrected as shown below:

| | |
|---|---|
| Col. 1, line 13 | "iscloses" should read --discloses--. |
| Col. 1, line 17 | "pyridinyl)" should read --5-(pyridinyl)--. |
| Col. 3, line 42 | "salts" should read --salt--. |
| Col. 4, line 38 | Line 38 should read: --trile is converted to 3-nitro-5-hetero-2(1H)-pyridone via 5-hetero- --. |
| Col. 6, line 3 | "catatria" should read --cat atria--. |

Signed and Sealed this

Nineteenth Day of August 1986

[SEAL]

Attest:

DONALD J. QUIGG

Attesting Officer

Commissioner of Patents and Trademarks